United States Patent [19]

Tsurushima et al.

[11] Patent Number: 4,577,012

[45] Date of Patent: Mar. 18, 1986

[54] METHOD OF SEPARATION OF NUCLEOTIDES AND NUCLEOSIDES FROM EACH OTHER

[75] Inventors: Masaaki Tsurushima, Minoo; Gozi Kokubu, Kitakatsuragi; Koji Moriya, Osaka, all of Japan

[73] Assignee: Takeda Chemical Industries, Ltd., Osaka, Japan

[21] Appl. No.: 557,367

[22] Filed: Dec. 2, 1983

[30] Foreign Application Priority Data

Dec. 3, 1982 [JP] Japan ................. 57-212971

[51] Int. Cl.$^4$ .......... C07H 17/00; C07H 15/12; C07H 19/06
[52] U.S. Cl. ...................... 536/24; 536/23; 536/26; 536/27; 536/28; 536/29
[58] Field of Search .......... 536/23, 24, 26, 27, 536/28, 29; 424/180, 181

[56] References Cited

U.S. PATENT DOCUMENTS

| 3,120,511 | 2/1964 | Tanaka et al. | 260/211.5 |
| 3,382,231 | 5/1968 | Hirahara et al. | 536/24 |
| 3,413,282 | 11/1968 | Yoshikawa et al. | 536/23 |
| 3,493,558 | 2/1970 | Samejima et al. | 536/27 |

FOREIGN PATENT DOCUMENTS

| 722157 | 11/1965 | Canada | 536/29 |
| 1803978 | 5/1970 | Fed. Rep. of Germany | 536/26 |
| 0395049 | 4/1964 | Japan | 536/24 |
| 39-26858 | 11/1964 | Japan | 536/26 |
| 3995 | 3/1965 | Japan | 536/28 |
| 40-23510 | 10/1965 | Japan | 536/26 |
| 41-16063 | 9/1966 | Japan | 536/24 |
| 42-15114 | 8/1967 | Japan | 536/24 |
| 24181 | 10/1968 | Japan | 536/29 |

OTHER PUBLICATIONS

Buday et al., Use of Activated Carbon for the Recovery and Concentration of Nucleic Acid Derivative and Other Compounds for Biological Samples, Chem. Abs. 81:167775r, (1974).

Ohsawa et al., Separation of Nucleic Acid-Related Substances with Active Carbon, Chem. Abstracts 83:114833t, (1975).

Myasoedav, et al., Introduction . . . IV, Use of Activated Carbon for the Desalting of Tritium-Labelled Components of Nucleic Acids, Chem. Abs. 95:133289j, (1981).

Ternovii et al., Porous Structure of Activated Carbons as a Criterion in the Analysis of Molecular Hemosorption Mechanisms and in the Choice of Hemosorbent, Chem. Abs. 99:207472v, (1983).

Iijima et al., Formed Granular Activated Carbon, Chem. Abstracts 85:80434n, (1975).

Ukita, *Nucleic Acids, Nucleosides and Nucleotides*, pp. 142–146, (1965).

Yoshikawa et al., *Experimental Method with Metablolism of Phosphoric Acids*, pp. 195–197, (1958).

*Primary Examiner*—Ethel G. Love
*Attorney, Agent, or Firm*—Wenderoth, Lind & Ponack

[57] ABSTRACT

The industrially favored separation of nucleotides and nucleosides from a solution containing both of them can be conducted by contacting said solution, after adjusted to a pH of not higher than 7, with activated carbon to adsorb the nucleosides and nucleotides and then eluting the nucleotides with an aqueous solution of an alkali metal hydroxide.

11 Claims, No Drawings

METHOD OF SEPARATION OF NUCLEOTIDES AND NUCLEOSIDES FROM EACH OTHER

The present invention relates to an industrial method which separates efficiently nucleotides and nucleosides from each other. Nucleotides are valuable substances as a seasoning or a raw material for pharmaceuticals.

Generally, production of nucleotides is conducted by (1) a process which comprises allowing 5′-phosphodiesterase to act on ribonucleic acid (RNA) to conduct a hydrolysis and fractionating and purifying the objective nucleotides from the resulting solution, (2) a process which comprises effecting a nucleoside fermentation using starch, etc. as a raw material and phosphorylating the resulting nucleosides chemically or by use of an enzyme to yield nucleotides, (3) a process which comprises producing directly nucleotides by fermentation using saccharides and phosphates, and so forth. In these production processes, however, the step of separating and removing nucleosides which coexist as compounds analogous to the objective nucleotides is required in order to obtain such nucleotides.

As the separation method of nucleotides and nucleosides from each other, there have been known so far the methods utilizing ion exchange resins, decolorizing resins or activated carbon, but such conventional methods all suffer from the following defects.

Thus, the method utilizing ion exchange resins, which involves the adsorption of whole nucleic-acid related substances on resin and subsequent fractionation by the chromatographic technique (Tyunosin Ukita; "Nucleic Acids, Nucleosides and Nucleotides", published by Asakura Shoten, pp. 142–146, 1965), is not considered suitable for an industrial separation and purification method in that it requires an enormous amount of adsorbent to be used as compared with that of the substance to be adsorbed, costs a great deal for concentration owing to extreme diluteness of the resulting eluate and does not always provide excellent separation performance for each component substance.

As the method utilizing decolorizing resins as adsorbent, there have been known a method which involves the selective adsorption of nucleotides (The Japanese Patent Publication No. 3995/1965) and a method which comprises adsorbing whole nucleic-acid related substances on the resins and then fractionating them chromatographically (The Japanese Patent Publication No. 24181/1968), but these methods are also not satisfactory as an industrial separation and purification method for the same reasons as described above with the method utilizing ion exchange resins.

On the other hand, a method which comprises adsorbing nucleotides with activated carbon and separating them chromatographically is known, but according to such conventional method, it is easy to adsorb nucleotides but difficult to elute them (Haruhisa Yoshikawa and Taijo Takahashi; "Experimental Method with Metabolism of Phosphoric Acids" published by Hirokawa Shoten, pp. 195, 1958).

For lessening the difficulty, as a special eluting agent such as alcoholic ammonia is used in the elution, another step of effecting ion exchange, etc. must be added to obtain nucleotides as the desired alkali metal salt, and normally, nucleotides are eluted in a by far more diluted form than before treatment. Therefore, the method requires the complex subsequent step of isolation and encounters many difficulties as an industrial separation and purification method.

Under these circumstances, the present inventors conducted extensive investigation into the conventional separation method utilizing activated carbon in terms of properties of solution to be treated, components and concentration of eluting agent, etc., and as a result, found that when a solution containing nucleotides and nucleosides is adjusted to a pH of not more than 7 and contacted with activated carbon to adsorb the nucleotides and nucleosides, followed by elution with an aqueous solution of an alkali metal hydroxide, the nucleotides are selectively eluted and separated, and that when elution is effected then with an aqueous solution containing an alkali metal hydroxide and a lower alcohol, the nucleosides are easily eluted and recovered, thereby attaining separation of nucleotides and nucleosides from each other. The finding has culminated in the present invention.

Thus, the present invention is directed toward a method of separation of nucleotides and nucleosides from each other, which comprises contacting a solution containing nucleosides and nucleotides, after adjusted to a pH of not more than 7, with activated carbon to adsorb the nucleosides and nucleotides and then eluting the nucleotides with an aqueous solution of an alkali metal hydroxide.

The method of the present invention can be applied to every solution, only if it contains nucleotides and nucleosides and is adjusted to a pH of not more than 7. Examples of such solution include hydrolysis solutions of yeast nucleic acids, etc., extracts of animal tissues, fermentation solutions of substances related to nucleic acids, reaction solutions resulting from phosphorylating nucleosides chemically or with enzymes, and liquids of each of intermediary steps for separating and obtaining the objective nucleotides from such solutions, provided, however, that all of them contain nucleotides and nucleosides.

The term "nucleotide" as used herein denotes mono-, di- and triphosphates, or their corresponding deoxyribose homologs, of purine and pyrimidine nucleosides such as inosine, guanosine, adenosine, xanthosine, cytidine and uridine. Their examples include inosine-5′-monophosphate, guanosine-5′-monophosphate, adenosine-5′-monophosphate, xanthosine-5′-monophosphate, cytidine-5′-monophosphate, uridine-5′-monophosphate, deoxyadenosine-5′-monophosphate, deoxyadenosine-5′-monophosphate, deoxycytidine-5′-monophosphate, deoxyuridine-5′-monophosphate, inosine-2′(3′),5′-diphosphate, inosine-5′-diphosphate, guanosine-2′(3′),5′-diphosphate, guanosine-5′-diphosphate, adenosine-2′(3′),5′-diphosphate, adenosine-5′-diphosphate, cytidine-5′-diphosphate, uridine-5′-diphosphate, deoxyadenosine-5′-diphosphate, deoxyadenosine-5′-diphosphate, deoxycytidine-5′-diphosphate, deoxyuridine-5′-diphosphate, adenosine-5′-triphosphate, guanosine-5′-triphosphate, deoxyadenosine-5′-triphosphate, deoxyguanosine-5′-triphosphate, deoxycytidine-5′-triphosphate, deoxyuridine-5′-triphosphate, inosine-2′-monophosphate, guanosine-3′-monophosphate, adenosine-3′,5′-cylic monophosphate, and xanthine-2′,3′-cyclic monophosphate. These nucleotides may be contained in not less than two kinds in a solution.

On the other hand, examples of the nucleoside include purine and pyrimidine nucleosides, such as inosine, guanosine, adenosine, xanthosine, cytidine, uridine, thymidine and orotidine, as well as 5-amino-4- imidazolecarboxyamidoriboside (hereinafter referred to briefly as "AICAR") or deoxy ribose homologs corresponding to these compounds. Although AICAR and its deoxyribose homologs normally are not treated as nucleoside, these compounds are treated as compounds similar to nucleosides from the standpoints of organic chemistry and biochemistry, and the method of the present invention can be applied to these compounds in the same manner as to the other nucleosides. In this specification, therefore, it is to be understood that AICAR and its deoxyribose homologs are included in the scope of nucleosides.

The method of the present invention can be applied regardless of the content ratio of nucleotide to nucleoside, and favorably applied, for example, to solutions containing about 0.1 to 100 parts, preberably 0.1 to 20, more preferably 0.1 to 10 parts, by weight of nucleosides against 100 parts by weight of nucleotides.

In applying the present invention, it is normally preferable that nucleotides and nucleosides, with their contents below the saturation solubilities at a pH of not more than 7, are completely dissolved in a solution to be treated. In the case of nucleoside, however, the content does not always need to be not more than the saturation solubility, and nucleosides may be suspended normally in quantities within the range of about 0.1 to 2 g per l of solution to be treated, which depends upon the kinds and shape of activated carbon, method of contacting with a solution to be treated, etc. The suspended nucleosides in such amount range, when a solution to be treated is for example passed through a column packed with activated carbon, are filtered through but get accumulated on the uppermost layer, but in the subsequent elution step, are once dissolved and adsorbed, thereafter acting similarly together with the dissolved component in the solution to be treated.

As the method of adjusting the pH of a solution to not more than about 7, the pH may be brought to the desired pH value of not more than 7 by addition of inorganic acids normally employed such as hydrochloric acid and sulfuric acid or by treatment with cation exchange resins, etc., in the case of the pH of the raw solution exceeding 7. When the pH of the raw solution is less than 7, the method of the present invention can be applied without adjustment of the pH required, but because the adsorbed amount of nucleotides and nucleosides onto activated carbon normally increases with decreasing pH value, it is advisable to adjust the pH preferably to not more than 3, more preferably to not more than 1, with the use of the above mentioned inorganic acids or cation exchange resins, etc.

The activated carbon, which is useful in the present invention, is not particularly limited, and is exemplified by activated carbon exhibiting such pore characteristics as not less than 0.6 cc/g of a total pore volume occupied by pores having a diameter of not more than $15\mu$, not less than 0.4 cc/g of a total pore volume occupied by pores having a diameter of not more than 300 Å and not less than 17 Å of an average pore diameter for pores having a diameter of not more than 300 Å.

Out of the above pore characteristics, the total pore volume occupied by pores having a diameter of not more than $15\mu$ is measured for example by the methods such as mercury intrusion method and nitrogen gas adsorption methods [Keii Tominaga: "Adsorption", pp. 95 to 113 (1967), published by Kyoritsu Publishing Co.]. The total pore volume occupied by pores having a diameter of not more than 300 Å is determined for example by the nitrogen gas adsorption method (the method as described in the above literature) and the like. The average pore diameter for pores having a diameter of not more than 300 Å is calculated from the pore volume for pores having a diameter of not more than 300 Å, which are assumed to be cylindrical, and the specific surface area as computed by the BET equation (the method described in the above literature) based on the adsorption isotherm for a nitrogen gas.

Average pore diameter $=4\times$(pore volume)/(specific surface area)

where it should be noted that the pore volume in the above equation denotes the total pore volume occupied by pores having a diameter of not more than 300 Å.

The activated carbon exhibiting the particular pore characteristics as described above is obtained for example by (1) immersing wooden raw materials such as wood pieces, sawdust and fruit shells (coconut shells) in chemical agents such as zinc chloride, phosphoric acid and calcium chloride, burning at temperatures of about 600 to 700° C. and eliminating and washing the added chemical agents with acids such as hydrochloric acid, or by (2) treating mineral based raw materials such as coal, distillation residue of petroleum, petroleum coke, fruit shells (coconut shells) and petroleum pitch with acids or alkalis, and activating at temperatures of 750° to 1050° C. with steam, carbon dioxide gas, etc.

The activated carbon may be powdery, grain-like or granular, and the latter two forms are preferred; for example, the granular activated carbon containing not less than 90% of granules with the grain size of 8 to 250 mesh, whereby the above mesh is in accordance with the criteria as stipulated by the Japan Industrial Standard (JIS).

Specific examples of the above activated carbon include Tokusei Shirasagi for chromatographic uses, Ryujo (granular) Shirasagi KL, Ryujo (granular) Shirasagi W, Ryujo (granular) Shirasagi C₂C and Kyujo (spherical) Activated Carbon X-7100 (all produced by Takeda Chemical Ind., Ltd. of Japan), CAL (produced by Calgon Corporation of U.S.A.) and Diahope 008, spherical activated carbon (produced by Mitsubishi Chemical Ind., Ltd. of Japan).

The method of the present invention is conducted in practice by contacting a solution (solution to be treated) containing nucleotides and nucleosides, after being adjusted to a pH of not more than about 7, with activated carbon to adsorb the nucleotide and nucleoside, and eluting the nucleotides with a solution of an alkali metal hydroxide.

As the means of contacting a solution to be treated with activated carbon, by way of example, there may be mentioned means such as the contact filtration method, fixed-bed adsorption method, moving-bed adsorption method and fluidized-bed adsorption method. Among others, the fixed-bed adsorption method such as a means which comprises packing activated carbon into a column and passing a solution to be treated through the column from its top or bottom is industrailly advantageous in terms of easiness and adsorption efficiency. When activated carbon is used by packing into a column as described above, furthermore, such procedure can offer advantages in that the excellent separation performance of nucleotides from nucleosides is realized in the subsequent desorption step.

The amount of activated carbon to be used varies depending upon its type, and suitably ranges from about 10 to 20 times the total amount of nucleotides and nucleosides in a solution to be treated. However, it is desirable to measure in advance the maximum limiting amount ensuring the prevention of nucleotide leaking through a solution-passing test and to determine a feeding amount for nucleotides and nucleosides. In addition, it is preferable to maintain the temperature inside the activated carbon column at room temperature or not higher than room temperature, because the adsorption amount increases on the side of lowered temperatures.

By passing a solution to be treated through a column following the above procedure, the nucleotides and nucleosides are adsorbed onto activated carbon, while, on the other hand, impurities in the solution to be treated such as inorganic acids exemplified by phosphoric acid, hydrochloric acid and sulfuric acid and their inorganic salts are removed in the effluent.

Subsequently, the activated carbon having adsorbed the nucleotides and nucleosides is contacted with an aqueous solution of an alkali metal hydroxide, and by this procedure, the nucleotides can be selectively eluted. As the alkali metal hydroxide, by way of example, favorable use can be made of sodium hydroxide and potassium hydroxide, and they may either be selected depending upon the type of a salt desired for the nucleotides. Their concentration suitably ranges from about 0.2 to 1.5 normal. When the concentration fails to reach the lower limit of the range, elution of the nucleotides becomes imcomplete, and when it exceeds the upper limit, elution of the nucleosides is often brought about. The elution is normally carried out at a temperature near room temperature, but it is in some instances preferred to heat at about 50° C. to 80° C. according to the type of activated carbon used.

By the above procedure, the nucleotides can be separated from a solution containing nucleotides and nucleosides. From the eluate containing the nucleotides as obtained in this manner, the nucleotides can be obtained by conducting suitably the isolation and purification methods for nucleotides normally employed such as pH adjustment, ion exchange, evaporation, concentration, crystallization through cooling or addition of water-soluble organic solvents, salting out, filtration and centrifugation.

After elution of the nucleotides, on the other hand, elution of the nucleosides adsorbed on activated carbon can be conducted by contacting with an aqueous solution containing an alkali metal hydroxide and a lower alcohol. Examples of the alkali metal hydroxide include sodium hydroxide and potassium hydroxide. As the lower alcohol, use can be made of all of alcohols having not more than four carbon atoms, such as methanol, ethanol, propanol, isopropanol, n-butanol, sec-butanol, tert-butanol and isobutanol, in one or not less than two kinds.

The concentrations of the alkali metal hydroxide and lower alcohol are not particularly limited, and normally, both are preferably not less than about 0.5% in order to facilitate the elution of the nucleosides. They may be suitably selected within the range up to the saturation solubility in water according to the types of nucleoside and activated carbon, etc. The elution temperature may be in the neighborhood of room temperature, but it is normally preferable to heat at about 50° C. to 80° C., because it facilitates the elution of the nucleosides.

In cases in which the method of the present invention is conducted into practice by use of activated carbon packed into a column, an alkali metal hydroxide and a lower alcohol are normally mixed in advance of the passing of a solution, although it is feasible to resort to an expedient of introducing them into a column simultaneously or separately in a successive way so that they may be mixed in the column.

From the eluate containing the nucleosides as obtained in this manner, the nucleosides can be obtained by conducting suitably the isolation and purification methods for nucleosides normally employed such as pH adjustment, ion exchange, evaporation, crystallization through cooling or addition of water-soluble organic solvents, salting-out, filtration and centrifugation. The nucleosides thus recovered may be subjected to production of nucleotides by the conventional methods.

The method of the present invention permits the industrially favored separation of nucleotides and nucleosides from a solution containing both of them. Though nucleotides are normally made commercially available for demands in the form of alkali metal salts, furthermore, the method of the present invention produces nucleotides in any desired alkali metal salts on the occasion of elution from activated carbon, and therefore can simplify the production processes as compared with the conventional methods. In addition, the method of the present invention, by selecting suitably the component concentration in an eluting agent, can perform the separation through elution of nucleotides and nucleosides both in the more concentrated state than in a solution to be treated, and is therefore considered the industrially favored method in that it can effect the separation through elution and the concentration simultaneously.

The examples are described below to illustrate the present invention in more detail.

EXAMPLE 1

A liquid containing 5'-nucleotides as obtained by treating a commercially available ribonucleic acid with enzymes (5'-phosphodiesterase and 5'-adenylate deaminase) was filtered in the presence of a filter aid (Hyflosupercel ®, Manvill Export Cooperation, U.S.A.) and then treated with Amberlite IR-120 ®, a cation exchange resin. The liquid was found to contain 6.14 mg/ml of 5'-inosinic acid, 6.46 mg/ml of 5'-guanylic acid, 5.74 mg/ml of 5'-uridylic acid, 4.45 mg/ml of 5'-cytidylic acid, 0.119 mg/ml of inosine, 0.130 mg/ml of guanosine, 0.051 mg/ml of hypoxanthine and 0.056 mg/ml of guanine and to show pH 2.3. 10 l of the liquid was passed through a column of 60 mm inner diameter packed with granular activated carbon CAL ® to the packing height of 180 cm at 5° C. over the period of 3 hours to adsorb the nucleic-acid related substances inclusive of 5'-inosinic acid. After the packed activated carbon was washed thoroughly with water, 5 l of a 2% aqueous sodium hydroxide solution was passed through the column, and then 5 l of water was introduced to elute the nucleotides (eluate 1). Subsequently, 4 l of an aqueous solution containing 20 g of sodium hydroxide and 300 g of isobutyl alcohol was passed through the column, and then, 6 l of water was introduced to elute the nucleosides (eluate 2). The amounts of respective nucleic acid related substances as recovered in the eluates are as shown in the following Table.

| Nucleic acid re-lated substance | Content in starting solution (g) | Eluate 1 | | Eluate 2 | |
|---|---|---|---|---|---|
| | | Yield (g) | Recovery (%) | Yield (g) | Recovery (%) |
| 5'-inosinic acid | 61.4 | 60.8 | 99 | 0.4 | 0.7 |
| 5'-guanylic acid | 64.6 | 63.3 | 98 | 0.6 | 0.9 |
| 5'-uridylic acid | 57.4 | 56.8 | 99 | 0.5 | 0.9 |
| 5'-cytidylic acid | 44.5 | 43.2 | 97 | 0.8 | 1.8 |
| inosine | 1.19 | 0.07 | 6 | 1.11 | 93 |
| guanosine | 1.30 | 0.05 | 4 | 1.24 | 95 |
| hypoxanthine | 0.51 | 0.36 | 71 | 0.14 | 27 |
| guanine | 0.56 | 0.46 | 82 | 0.09 | 16 |
| Total | 10 l | 10 l | | 10 l | |

EXAMPLE 2

Phosphorus oxychloride was dissolved in trimethyl phosphate, to which, after addition of a small amount of water, commercially available inosine and guanosine were added. After the reaction was conducted at room temperature for 3 hours under stirring, the reaction solution was poured into ice-cooled water to conduct hydrolysis (Refer to the Japanese Patent Publication No. 11071/1967), and the trimethyl phosphate was separated by extraction with 1,2-dichloroethane. The raffinate was found to contain 3.13% of 5'-inosinic acid, 3.09% of 5'-guanylic acid, 0.16% of inosine, 0.23% of guanosine, 0.013% of hypoxanthine and 0.030% of guanine as well as phosphoric acid and hydrogen chloride, and to exhibit a pH of 0.15. 10 l of the solution was passed through a column of 100 mm in diameter packed with Diahope ® 008, granular activated carbon, to the packing height of 90 cm at 10° C. over the period of 3 hours to adsorb the nucleic acid related substances inclusive of 5'-inosinic acid. After the packed activated carbon was washed thoroughly with water, 8 l of a 4% aqueous solution of sodium hydroxide was passed through the column, while maintaining the inside of the column at 60° C., and subsequently 10 l of water was introduced to elute the nucleotides, etc. (eluate 1). Then, an aqueous solution containing 60 g of sodium hydroxide and 1000 g of isopropyl alcohol was passed through the column, and 12 l of water was introduced to elute the nucleosides, etc. (eluate 2). The amounts of respective nucleic acid related substances as recovered in the eluates are as shown in the following Table.

| Nucleic acid re-lated substance | Content in starting solution (g) | Eluate 1 | | Eluate 2 | |
|---|---|---|---|---|---|
| | | Yield (g) | Recovery (%) | Yield (g) | Recovery (%) |
| 5'-inosinic acid | 313 | 311 | 99 | 1.7 | 0.5 |
| 5'-guanylic acid | 309 | 306 | 99 | 2.1 | 0.7 |
| inosine | 16 | 0.8 | 5 | 15 | 94 |
| guanosine | 23 | 0.5 | 2 | 22 | 96 |
| hypoxanthine | 1.3 | 1.0 | 77 | 0.3 | 23 |
| guanine | 3.0 | 2.7 | 90 | 0.3 | 10 |
| Total | 10 l | 18 l | | 18 l | |

EXAMPLE 3

Guanosine was reacted with phosphorus oxychloride in the solvent of acetone in the presence of a small amount of water at 5° C. for 6 hours, and the reaction mixture was lyophilized at −70° C. to distill off the excessive phosphorus oxychloride and acetone. Ice-cooled water was added to the resultant residue to dissolve, and the solution was adjusted to pH 1.5 by the addition of sodium hydroxide, followed by heating at 70° C. for 30 minutes and then cooling rapidly at 5° C. The aqueous solution thus obtained was found to contain 5.81% of 5'-guanylic acid, 0.85% of guanosine and 0.091% of guanine (Refer to the Japanese Patent Publication No. 18319/1965).

10 l of the solution was passed through a column of 100 mm in diameter packed with granular activated carbon Shirasagi ® KL to the packing height of 90 cm at 5° C. over the period of 4 hours to adsorb the nucleic-acid related substances inclusive of 5'-guanylic acid. After the packed activated carbon was washed thoroughly with water, 12 l of a 2% aqueous solution of sodium hydroxide was passed through the column, and then 10 l of water was introduced to elute 5'-guanylic acid, etc (eluate 1). Subsequently, 6 l of an aqueous solution containing 40 g of sodium hydroxide and 2000 g of methanol was passed through the column, and then 12 l of water was introduced to elute guanosine, etc. (eluate 2). The amounts of respective nucleic acid related substances as recovered in the eluates are as shown in the following Table.

The eluate (1) was adjusted to pH 8 with hydrochloric acid, concentrated under reduced pressure, treated with activated carbon for decolorization use and added dropwise to aqueous methanol. The crystals which crystallized out were recovered by filtration to give 640 g of heptahydrate of disodium 5'-guanylate. On the other hand, the eluate (2) was adjusted to pH 7.5 with hydrochloric acid, treated with activated carbon for decolorization use and concentrated under reduced pressure. The crystals, which crystallized out, were recovered by filtration to recover 76 g of guanosine with a purity of 97%.

| Nucleic acid re-lated substance | Content in starting solution (g) | Eluate (1) | | Eluate (2) | |
|---|---|---|---|---|---|
| | | yield (g) | Recovery (%) | Yield (g) | Recovery (%) |
| 5'-guanylic acid | 581 | 569 | 98 | 6 | 1.0 |
| guanosine | 85 | 2.6 | 3.1 | 82 | 96 |
| guanine | 9.1 | 6.8 | 75 | 1.8 | 20 |
| Total | 10 l | 22 l | | 18 l | |

EXAMPLE 4

A liquid containing 5'-nucleotides as obtained by treating a commercially avairable ribonucleic acid (Crude Nucleic Acid KRNA, Kojin Co., Japan) with the enzyme solution containing 5'-phosphodiesterase and 5'-adenylate deaminase, which are obtained by culturing *Streptomyces aureus,* was filtered in the presence of a filter aid (Hyflosuper-cel ®, Manvill Export Cooperation, U.S.A.), and then treated with a cation exchange resin (Amberlite ® IR-120, Rohm and Haas, U.S.A.).

The liquid was found to contain 5.17 mg/ml of 5'-inosinic acid, 5.00 mg/ml of 5'-guanylic acid, 5.61 mg/ml of 5'-uridylic acid, 3.14 mg/ml of 5'-cytidylic acid, 0.132 mg/ml of inosine, 0.153 mg/ml of guanosine, 0.064 mg/ml of hypoxanthine and 0.068 mg/ml of guanine, and 1.19 mg/ml of inorganic acid besides and to show pH 2.1. 10 l of the liquid was passed through a column of 50 mm inner diameter packed with an activated carbon (Ryujo Shirasagi ® C2c) to the packing height of 65 cm at 5° C. over 6 hours to adsorb the nucleic acid related substances inclusive of 5'-inosinic acid. After the packed activated carbon was washed thoroughly with water, 2 l of a 2% aqueous sodium hydroxide solution was passed through the column, and then 2 l of water was introduced to elute the nucleotides, etc. (eluate 1).

Subsequently, 2 l of an aqueous solution containing 100 g of sodium hydroxide and 500 g of ethanol was passed through the column, and then, 2 l of water was introduced to elute the nucleosides, etc. (eluate 2). The amounts of respective nucleic acid related substances as recovered in the eluates are as shown in the following Table.

| Nucleic acid related substance | Content in starting solution (g) | Eluate 1 Yield (g) | Eluate 1 Recovery (%) | Eluate 2 Yield (g) | Eluate 2 Recovery (%) |
|---|---|---|---|---|---|
| 5'-inosinic acid | 51.7 | 50.7 | 98 | 0.5 | 1.0 |
| 5'-guanylic acid | 50.0 | 49.0 | 98 | 0.4 | 0.8 |
| 5'-uridylic acid | 56.1 | 55.5 | 99 | 0.2 | 0.4 |
| 5'-cytidylic acid | 31.4 | 30.8 | 98 | 0.3 | 1.0 |
| inosine | 1.32 | 0.06 | 5 | 1.24 | 94 |
| guanosine | 1.53 | 0.09 | 6 | 1.42 | 93 |
| hypoxanthine | 0.64 | 0.44 | 69 | 0.19 | 30 |
| guanine | 0.68 | 0.60 | 88 | 0.07 | 10 |
| phosphoric acid | 11.9 | 0.2 | 2 | 0.01 | 0.1 |
| Total | 10 l | 4 l | | 4 l | |

What we claim is:

1. A method for the separation of nucleotides and nucleosides from each other, which comprises contacting a solution containing nucleotides and nucleosides, after being adjusted to a pH of not more than 7, with activated carbon to absorb the nucleosides and nucleotides and then eluting the nucleotides with an aqueous solution of an alkali metal hydroxide, the said nucleotides being from the group of inosine-5'-monophosphate, guanosine-5'-monophosphate, adenosine-5'-monophosphate, xanthosine-5'-monophosphate, cytidine-5'-monophosphate, uridine-5'-monophosphate, deoxyadenosine-5'-monophosphate, deoxycytidine-5'-monophosphate, deoxyuridine-5'-monophosphate, inosine-2'(3'),5'-diphosphate, inosine-5'-diphosphate, guanosine-2'(3'),5'-diphosphate, guanosine-5'-diphosphate, adenosine-2'(3'),5'-diphosphate, adenosine-5'-diphosphate, cytidine-5'-diphosphate, uridine-5'-diphosphate, deoxyadenosine-5'-diphosphate, deoxycytidine-5'-diphosphate, deoxyuridine-5'-diphosphate, adenosine-5'-triphosphate, guanosine-5'-triphosphate, deoxyadenosine-5'-triphosphate, deoxyguanosine-5'-triphosphate, deoxyctidine-5'-triphosphate, deoxyuridine-5'-triphosphate, inosine-2'-monophosphate, guanosine-3'-monophosphate, adenosine-3',5'-cyclic monophosphate, and xanthine-2',3'-cyclic monophosphate, the said nucleosides being inosine, guanosine, adenosine, xanthosine, cytidine, uridine, thymidine and orotidine and a deoxyribose homolog of said compounds and the said activated carbon having pore characteristics such that not less than 0.6 cc/g of the total pore volume is occupied by pores having a diameter of not more than 15µ, not less than 0.4 cc/g of the total pore volume is occupied by pores having a diameter of not more than 300 Å and not less than 17 Å of an average pore diameter for pores having a diameter of not more than 300 Å and, following the nucleotide elution, eluting the nucleosides with an aqueous solution containing an alkali metal hydroxide and a lower alcohol.

2. A method of separation of nucleotides and 5-amino-4-imidazolecarboxyamidoriboside from each other, which comprises contacting a solution containing nucleotides and 5-amino-4-imidazolecarboxyamidoriboside, after being adjusted to a pH of not more than 7, with activated carbon to absorbe 5-amino-4-imidazolecarboxyamidoriboside and nucleotides and then eluting the nucleotides with an aqueous solution of an alkali metal hydroxide, the said nucleotides being from the group inosine-5'-monophosphate, quanosine-5'-monophosphate, adenosine-5'-monophosphate, xanthosine-5'-monophosphate, cytidine-5'-monophosphate, uridine-5'-monophosphate, deoxyadenosine-5'-monophosphate, deoxycytidine-5'-monophosphate, deoxyuridine-5'-monophosphate, inosine-2'(3'),5'-diphosphate, inosine-5'-diphosphate, guanosine-2'(3'),5'-diphosphate, guanosine-5'-diphosphate, adenosine-2'(3'),5'-diphosphate, adenosine-5'-diphosphate, cytidine-5'-diphosphate, uridine-5'-diphosphate, deoxyadenosine-5'-diphosphate, deoxycytidine-5'-diphosphate, deoxyuridine-5'-diphosphate, adenosine-5'-triphosphate, guanosine-5'-triphosphate, deoxyadenosine-5'-triphosphate, deoxyguanosine-5'-triphosphate, deoxycytidine-5'-triphosphate, deoxyuridine-5'-triphosphate, inosine-2'-monophosphate, guanosine-3'-monophosphate, adenosine-3',5'-cyclic monophosphate, and xanthine-2',3'-cyclic monophosphate, and the said activated carbon having pore characteristics such that not less than 0.6 cc/g of the total pore volume is occupied by pores having a diameter of not more than 15µ, not less than 014 cc/g of total pore volume is occupied by pores having a diameter of not more than 300 Å and not less than 17 Å of an average pore diameter for pores having a diameter of not more than 300 Å and following the nucleotide elution, eluting the 5-amino-4-imidazolecarboxyamidoriboside with an aqueous solution containing an alkali metal hydroxide and a lower alcohol.

3. The method according to claim 1, wherein the solution containing nucleotides and nucleosides is a solution containing 0.1 to 100 parts by weight of nucleosides against 100 parts by weight of nucleotides.

4. The method according to claim 1, wherein the solution containing nucleotides and nucleosides is a solution containing 0.1 to 20 parts by weight of nucleosides against 100 parts by weight of nucleotides.

5. The method according to claim 1, wherein the solution containing nucleotides and nucleosides is a solution containing 0.1 to 10 parts by weight of nucleosides against 100 parts by weight of nucleotides.

6. The method according to claim 1, wherein the aqueous solution of an alkali metal hydroxide is 0.2-1.5N sodium hydroxide solution.

7. The method according to claim 1, wherein the pH of a solution containing nucleotides and nucleosides is adjusted to not more than 3.

8. The method according to claim 1, wherein the alkali metal hydroxide is sodium hydroxide.

9. The method according to claim 1, wherein the lower alcohol is methanol, ethanol, isopropanol or isobutanol.

10. The method according to claim 1, wherein the nucleotides are 5'-inosinic acid, 5'-guanylic acid, 5'-uridylic acid or 5'-cytidylic acid and the nucleosides are inosine or quanosine.

11. The method according to claim 1, wherein the nucleotides are 5'-inosinic acid or 5'-guanylic acid and the nucleosides are inosine or guanosine.

* * * * *